(12) United States Patent
Miller et al.

(10) Patent No.: US 6,713,640 B2
(45) Date of Patent: Mar. 30, 2004

(54) PROCESS FOR THE RECOVERY OF A POLYOL FROM AN AQUEOUS SOLUTION

(75) Inventors: Dennis J. Miller, Okemos, MI (US); James E. Jackson, Haslett, MI (US); Shubham P. Chopade, Florence, SC (US); Atulkumar D. Dhale, East Lansing, MI (US); Angela M. Clark, Greenwood, IN (US); Christopher W. Kiesling, Wyandotte, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/337,550

(22) Filed: Jan. 7, 2003

(65) Prior Publication Data

US 2003/0187281 A1 Oct. 2, 2003

Related U.S. Application Data

(62) Division of application No. 09/891,955, filed on Jun. 26, 2001, now Pat. No. 6,548,681.

(51) Int. Cl.[7] ............................................. C07D 317/10
(52) U.S. Cl. ....................................................... 549/430
(58) Field of Search .......................................... 549/430

(56) References Cited

U.S. PATENT DOCUMENTS 5,917,059 A    6/1999   Bruchmann et al.

OTHER PUBLICATIONS

Mahajani, S.M. et al., Reactive and Functional Polymers 28 29–38 (1995).
Tink, R.R., et al., Can. J. Technol. 29 243 (1951).
Broekhuis, R.R., et al., Ind. Eng. Chem. Res. 33 3230 1994.
Chopade, S.P. and Sharma, M.M., React Funct. Polym. 34 (1) 37 (1997).
Chopade, S., Reactive and Functional Polymers, 42 201 (1999).
Othmer, D., Ind. & Eng. Chem. 20 743 (1928).

*Primary Examiner*—Taofiq Solola
(74) *Attorney, Agent, or Firm*—Ian C. McLeod

(57) ABSTRACT

A process for the separation of a polyol or multiple polyols in admixture with other organic compounds, usually those produced with the polyol, is described. The process uses a distillation in a column (11) of a cyclic acetal from an aqueous solution which acetal is formed in a reaction mixture of the polyol and an aldehyde or ketone. The polyols, such as ethylene glycol and propylene glycol, are staple articles of commerce with many uses.

10 Claims, 11 Drawing Sheets

PROCESS FOR THE RECOVERY OF A POLYOL FROM AN AQUEOUS SOLUTION

CROSS-REFERENCE TO RELATED APPLICATION

This application is a divisional of application Ser. No. 09/891,955 filed Jun. 26, 2001 now U.S. Pat. No. 6,548,681.

STATEMENT REGARDING FEDERALLY FUNDED RESEARCH OR DEVELOPMENT

None

BACKGROUND OF THE INVENTION (1) Field of the Invention

The present invention relates to a process for the separation of a polyol from an aqueous solution. The process involves reactive distillation of the polyol as a cyclic acetal from an aqueous reaction mixture containing other organic compounds, particularly other polyols. In particular, the cyclic acetal is prepared by reaction of a ketone or aldehyde with the polyol along with distillation of cyclic acetal as it is formed from the reaction mixture.

(2) Description of the Related Art

There is a need to recover and purify polyols, including glycols, from an aqueous solution. These polyhydroxy compounds are typically formed in multistep processes in dilute aqueous solutions, from which the polyol(s) must be separated and purified before being used or sold. These processes include, but are not limited to, production of ethylene glycol and propylene glycol from their respective epoxides, formation of propylene glycol from glycerol, and formation of polyols via hydrogenolysis of sugars or sugar alcohols. All of these processes produce dilute mixtures of organic compounds including the desired polyols in the aqueous solution.

In the presence of acidic catalysts, glycols (or other polyols) react reversibly with aldehydes and ketones to form cyclic acetals. The reaction is known as acetalization or ketalization. The acetals of the polyols are far more volatile than the polyols themselves and much less polar, making them easily separable from water by distillation. Because the acetalization reaction is reversible, glycols and the aldehyde can be regenerated by acid hydrolysis of the acetal. The glycol can then be recovered and the aldehyde can be recycled. Ion exchange resins (IER) are one class of materials that can effectively catalyze acetal formation and hydrolysis, but mineral acids and other solid acids are effective as well. The reaction is as follows:

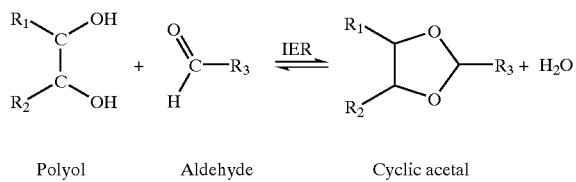

Polyol     Aldehyde     Cyclic acetal

Of general interest in connection with this type of reaction in a non-cyclic context is Mahajani, S. M. et al., Reactive And Functional Polymers 28 29–38 (1995).

There have been several reports of the reaction of glycols with aldehydes to form cyclic acetals. Tink and coworkers (Tink, R. R., et al., Can. J. Technol., 29, 243 (1951)) have published a series of papers describing recovery of aqueous glycerol solution via reactive extraction with various aldehydes. As disclosed, n-butyraldehyde and cyclohexanone were promising among the several aldehydes studied and the former was particularly selective. They also studied reactive extraction of several polyhydroxy compounds including D-sorbitol, adonitol, dulcitol, D-mannitol and ethylene glycol from aqueous solutions. High distribution coefficients were obtained with reactive extraction. For instance, with n-butyraldehyde the distribution coefficient for glycerol is 8.3, for EG is 5.9 and for D-sorbitol is 788.

Broekhuis et al. (Broekhuis, R. R., et al., Ind. Eng. Chem. Res., 33, 3230 (1994)) have compared the various routes for the recovery of propylene glycol from dilute aqueous solutions via reaction with aldehydes. They studied lower aldehydes, viz. formaldehyde and acetaldehyde, for reactive distillation and extractive reaction for the recovery. They have claimed to achieve 99+% recovery of propylene glycol in a reactive distillation process. One of the present inventors has reported on the recovery of ethylene glycol from aqueous solution via acetalization with formaldehyde (Chopade, S. P. and Sharma, M. M., React Funct. Polym. 34(1) 37 (1997)) using ion exchange resins as catalysts.

A search of the patent literature reveals no processes combining acetalization with reactive distillation of cyclic acetals for polyol separation. U.S. Pat. No. 5,917,059 to Bruchmann et al. describes preparation of the cyclic acetal compounds, but does not discuss them in context of a separation scheme for glycol recovery. There are numerous patents that describe inventions pertaining to acetals, acetalization, and reactive distillation, but none were found that pertained to a scheme for the recovery of polyols, especially from a dilute mixed solution of polyols, such as a sugar hydrogenolysis effluent.

Polyhydroxy compounds show a high affinity towards water and each other because of hydrogen bonding, and separation of these products from aqueous solution is conventionally done via a multi-column distillation process. In order to obtain ethylene glycol (EG) and propylene glycol (PG), water must be distilled off first because it has a lower boiling point temperature than the polyols. The energy to distill off water is the primary reason for the high cost of polyol separation and recovery. Separation of EG and PG (if they are present together) is also costly because they have very similar boiling points, so that a large number of stages and a large reflux ratio, translating to a large distillation column, is required to achieve the required purities. Purification of glycerol in a simple distillation column without forming poly-glycerides and decomposition products is impossible. Vacuum distillation, which has high operating costs, is the only distillation route for direct glycerol recovery.

Another approach for polyol recovery is solvent extraction of polyols from water. Glycols and glycerol have high affinity towards water (again because of hydrogen bonding), and it is difficult to find a suitable solvent with good distribution coefficient and low miscibility with water. Further, extraction only eliminates distillation of large amounts of water from the product stream. After extraction, there are distillation steps involving solvent recovery followed by separation of polyols from each other. Thus extraction is similar to distillation, except that water is replaced by a solvent.

There is a need for a safe and effective process for the production of polyols. In particular there is a need for a process to efficiently separate EG and PG from aqueous solutions.

OBJECTS

It is therefore an object of the present invention to provide an economical and efficient process for the separation of at least one polyol from water. It is further an object of the present invention to provide a process which is relatively easy to perform on a large scale suitable for commercial production of polyols such as EG and PG. These and other objects will become increasingly apparent by reference to the following description and the drawings.

SUMMARY OF THE INVENTION

The present invention relates to a continuous process for preparing at least one acetal from an aqueous solution containing at least one polyol and at least one other organic compound which comprises:

(a) reacting in a combination reaction and distillation vessel a reaction mixture of the polyol and an aldehyde or ketone containing 1 to 4 carbon atoms in the aqueous solution in the presence of an acid catalyst, wherein the reaction mixture is introduced into the reaction vessel containing the catalyst with a molar excess of the aldehyde or ketone over the polyol to produce the cyclic acetal in the aqueous solution; and (b) separating at least one cyclic acetal from the reaction mixture by distillation.

Further, the present invention relates to a continuous process for recovering a polyol from an aqueous solution containing other organic compounds which comprises:

(a) reacting in a combination reaction and distillation vessel a reaction mixture of the polyol and an aldehyde or ketone containing 1 to 4 carbon atoms in the aqueous solution, wherein the reaction mixture is continuously introduced into the vessel containing the catalyst with a molar excess of the aldehyde or ketone over the polyol to produce a cyclic acetal in the aqueous solution;

(b) separating the acetal from the mixture at elevated temperatures; and (c) hydrolyzing the cyclic acetal produced to recover the polyol as a liquid and the acetaldehyde or ketone which is separated as a vapor from the polyol.

Preferably the reaction mixture is at a temperature, less than the boiling point of the reaction mixture, at which at least the aldehyde or ketone is distilled from the reaction vessel as a distillate. Also, preferably if there is more than one cyclic acetal produced, the cyclic acetals are separated before the hydrolysis step is performed. The separation can be accomplished in the reaction vessel for the reactive distillation or in a separate vessel connected to the reaction vessel. Typically the reaction vessel(s) is a heated column. Preferably the desired cyclic acetal is also distilled from the reaction vessel and separated from the aldehyde or ketone.

Preferably the reaction mixture is at a temperature, less than the boiling point of the reaction mixture, at which at least the aldehyde or ketone is distilled from the aqueous solution as a distillate. Preferably the ketone or aldehyde is recycled.

DESCRIPTION OF PREFERRED EMBODIMENTS

Figure 1:
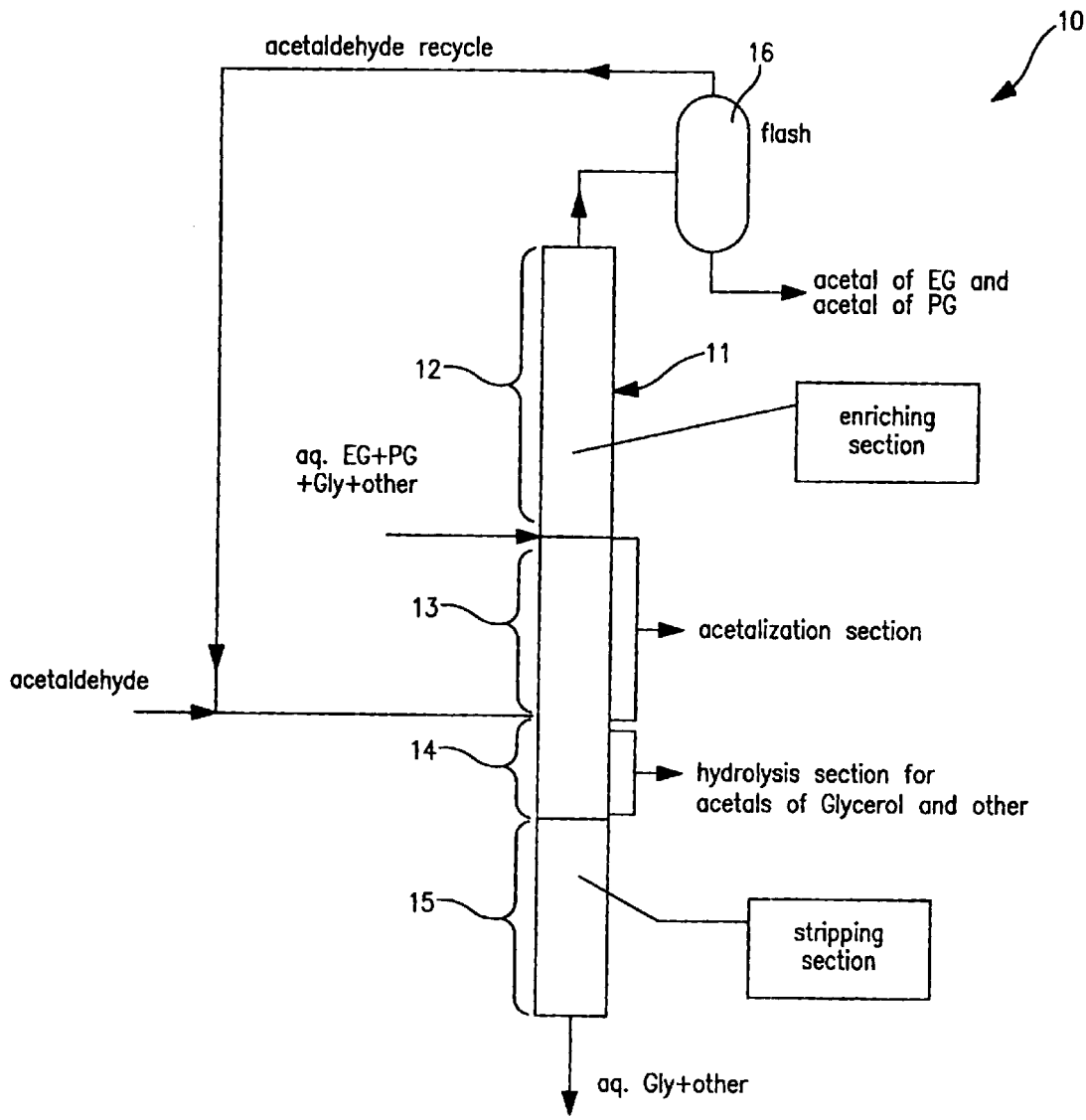
FIG. 1 is a schematic front view of a polyol recovery system 10 with a single reactive distillation column 11 for forming the cyclic acetal(s). EG is ethylene glycol, PG is propylene glycol, and Gly is glycerol.

The present invention relates to a process involving acetalization and reactive distillation of a polyol that takes advantage of the reversible reaction of the acetal which is formed and facilitates the separation and recovery of the polyol from an aqueous solution. The focus of the invention is on recovering ethylene and propylene glycols from aqueous solutions containing higher polyols, but the method has broader applications to recovery of a wide range of polyols from water. Boiling points of some acetals of interest for this process are given in Table 1.

TABLE 1

| Boiling points of some acetals and aldehydes | | | |
|---|---|---|---|
| Glycol | Aldehyde | Acetal | b.p., °C. |
| EG | Formaldehyde | 1,3-dioxolane | 74–75 |
| PG | Formaldehyde | 4-methyl-1,3-dioxolane | 84 |
| Glycerol | Formaldehyde | Glycerol formal | 191–195 |
| EG | Acetaldehyde | 2-methyl-1,3-dioxolane | 82–83 |
| PG | Acetaldehyde | 2,4-dimethyl-1,3-dioxolane | 91–93 |
| EG | Acetone | 2,2-dimethyl-1,3-dioxolane | 92–93 |
| PG | Acetone | 2,2,4-trimethyl-1,3-dioxolane | 98–99 |
| Glycerol | Acetone | | 188 |
| | Formaldehyde | | 101 |
| | Acetaldehyde | | 21 |
| | Isobutyraldehyde | | 64 |
| | Acetone | | 56 |

The reactive distillation process involves several distillation columns where the acetals are formed, separated from water, and subsequently hydrolyzed back to the desired polyol. The acetalization/reactive distillation scheme facilitates polyol recovery and purification at lower cost than conventional distillation or extraction methods. For the recovery of ethylene glycol and propylene glycol, acetals formed with formaldehyde or acetaldehyde have lower boiling points than water, so they can be removed once formed without having to boil off all the water present. This offers a large cost savings over conventional distillation. Further, these acetals have much lower boiling points than acetals of higher polyols such as glycerol, sorbitol and xylitol, which can be in potential feedstocks for EG/PG production, and acetals of process byproducts such as $C_4$ and $C_5$ polyols, so they are easily separated from the higher polyols and their acetals in solution. This aspect of the invention distinguishes it from the work of Broekhuis et al (1994) and Chopade and Sharma (1997), who did not consider recovery of EG and PG from mixed polyols. Further, the acetals of EG and PG can be separated from each other at much lower temperatures and potentially more easily than EG and PG themselves, so the cost of the polyol separation is substantially lower as well. Overall, the integration of the acetalization scheme into a biomass-based polyols process enhances the commercial usefulness of the process.

Ethylene glycol and propylene glycol are large-scale commodity chemicals: EG is produced at rate of 17 billion lb/yr and PG at about 1 billion lb/yr. The present invention provides a more energy efficient route for EG and PG recovery than the conventional distillation methods. This invention can be combined with the biomass-based production of EG and PG via sugar and sugar alcohol hydrogenolysis to provide an economical, renewable resource-based route to EG and PG production.

The preferred embodiment of the present invention is the recovery of EG and PG from a mixed polyols stream resulting from hydrogenolysis of sugars or sugar alcohols to polyols. The mixed polyol stream from hydrogenolysis contains, in addition to EG and PG, glycerol, unreacted feed ($C_5$ or $C_6$ sugar alcohol), and other organic compound byproducts such as $C_4$ polyols and lactic acid. Unreacted feed and byproducts are collectively referred to as "other organic compounds" hereinafter.

The choice of which acetal to form, e.g. which aldehyde or ketone to use to acetalize the diols to be recovered, has a strong affect on the configuration of the process. Formaldehyde was used in the initial feasability study. However, formaldehyde is a nuisance to the environment. Acetals can be formed with a large number of carbonyl compounds, but only acetaldehyde, formaldehyde, and acetone give acetals of PG and EG which have boiling points below that of water. Thus the preferred chemical for recovery of EG and PG is acetaldehyde. The boiling point of acetaldehyde is 21° C. and hence a closed system with a good chilling facility is required. The reactions can be carried out under pressure, if necessary, to enhance the acetaldehyde concentration in the liquid phase.

In reactive distillation, the potential exists for multiple reactions to take place in a single distillation column or, if desired, in multiple distillation columns. The use of a single column can lead to substantial savings in capital as well as operating cost. A schematic of a single column 11 reactive distillation process is shown in FIG. 1. FIG. 1 shows the system 10 including the reactive distillation column 11. The column 11 is divided into four sections to help understand the process concepts. The sections are the acetalization section 13, the enriching section 12, the hydrolysis section 14 and the stripping section 15. Sections 12 and 15, the enriching and stripping sections, respectively, are non-reactive, and there is no catalyst in these sections. Sections 13 and 14 are the reactive sections, which are the key sections in the process. The aqueous solution containing EG, PG, glycerol, and other products is fed at the top of section 13. Acetaldehyde is fed at a point where sections 13 and 14 meet. Acetaldehyde, being the most volatile component, moves up the distillation column through section 13. The aqueous feed moves down section 13 and reacts with acetaldehyde, forming acetals. The acetals of EG and PG, being more volatile than water, move up the column into non-reactive section 12. Section 12 strips water from the acetals and the acetals of EG and PG exit at the top of the column along with unreacted acetaldehyde.

Because there is essentially no acetaldehyde in section 14, the acetals of glycerol and other organic compounds will hydrolyze in the presence of catalyst back to glycerol and other organic compounds and acetaldehyde. Any acetaldehyde released will quickly move up the column 11 and glycerol and other products are recovered at the bottom of the column 11.

Figure 2:
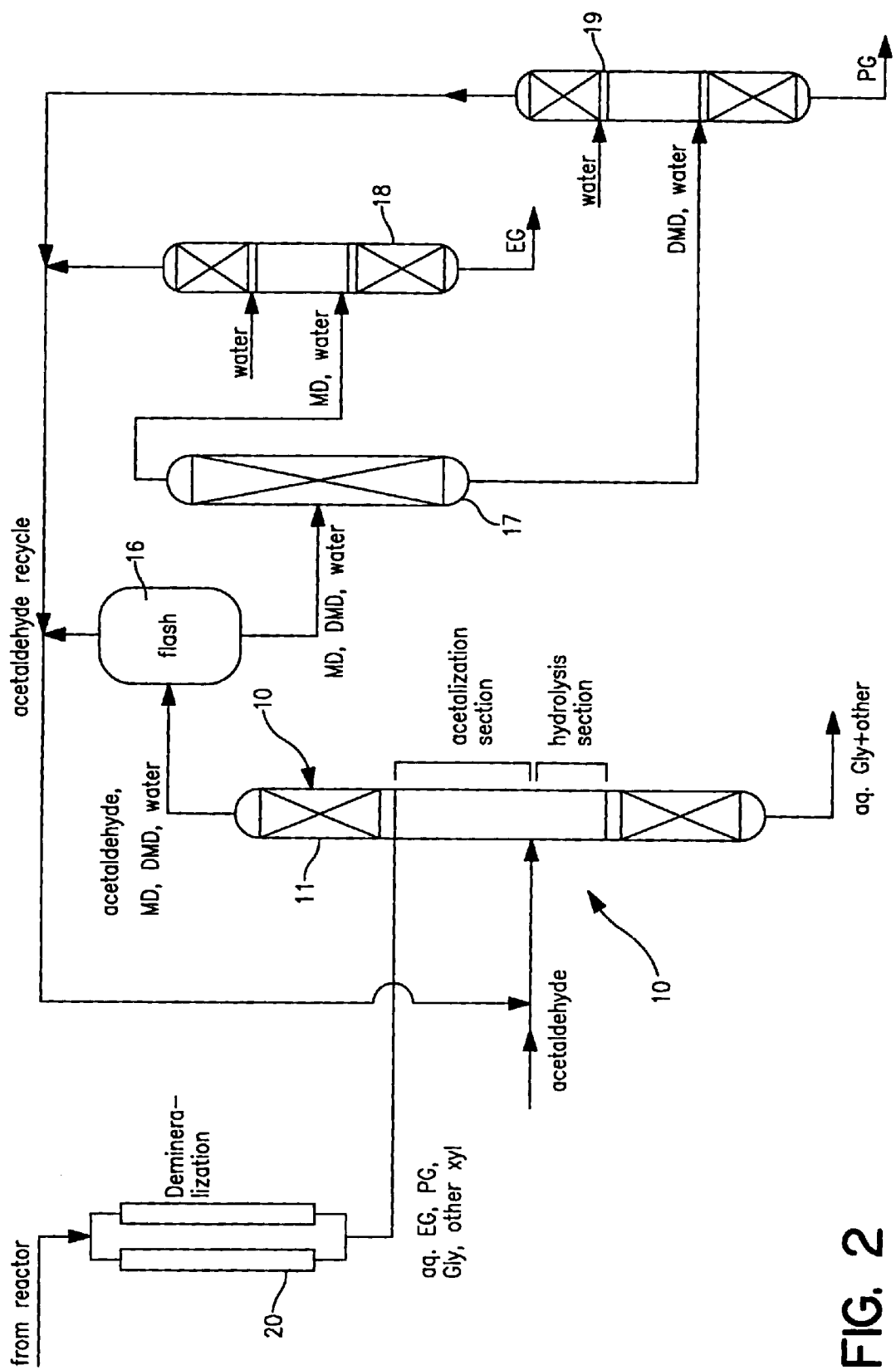
FIG. 2 is a schematic front view of the polyol recovery system 10 including reactive distillation column 11 and acetal hydrolysis and polyol recovery columns 18 and 19. MD is 2-methyl-1,3-dioxolane (acetal of EG), DMD is 2,4-dimethyl-1,3-dioxolane (acetal of PG).

FIG. 2 shows the column 11 in a reactive distillation system 10 with the separation of MD (2-methyl-1,3-dioxolane, which is the acetal of EG) and DMD (2,4-dimethyl-1,3-dioxolane, the acetal of PG). Flash drum 16 allows the separation of MD and DMD from acetaldehyde which is recycled. Column 17 separates 2MD from DMD. Recovery column 18 is for hydrolysis of MD and recovery column 19 is for hydrolysis of DMD. Vessel 20 is a demineralization vessel to remove inorganic compounds (salts, for instance) if present in the feed stream. Thus, in FIG. 2, acetaldehyde is separated from the acetals in the small column or flash drum 16 and is recycled back to the acetaldehyde feed to the column 11. The acetals are then separated from each other in the second column 17. Finally, each acetal is separately hydrolyzed back to its corresponding glycol (EG or PG) in the columns 18 and 19, and acetaldehyde is recycled back to column 11.

Figure 3:
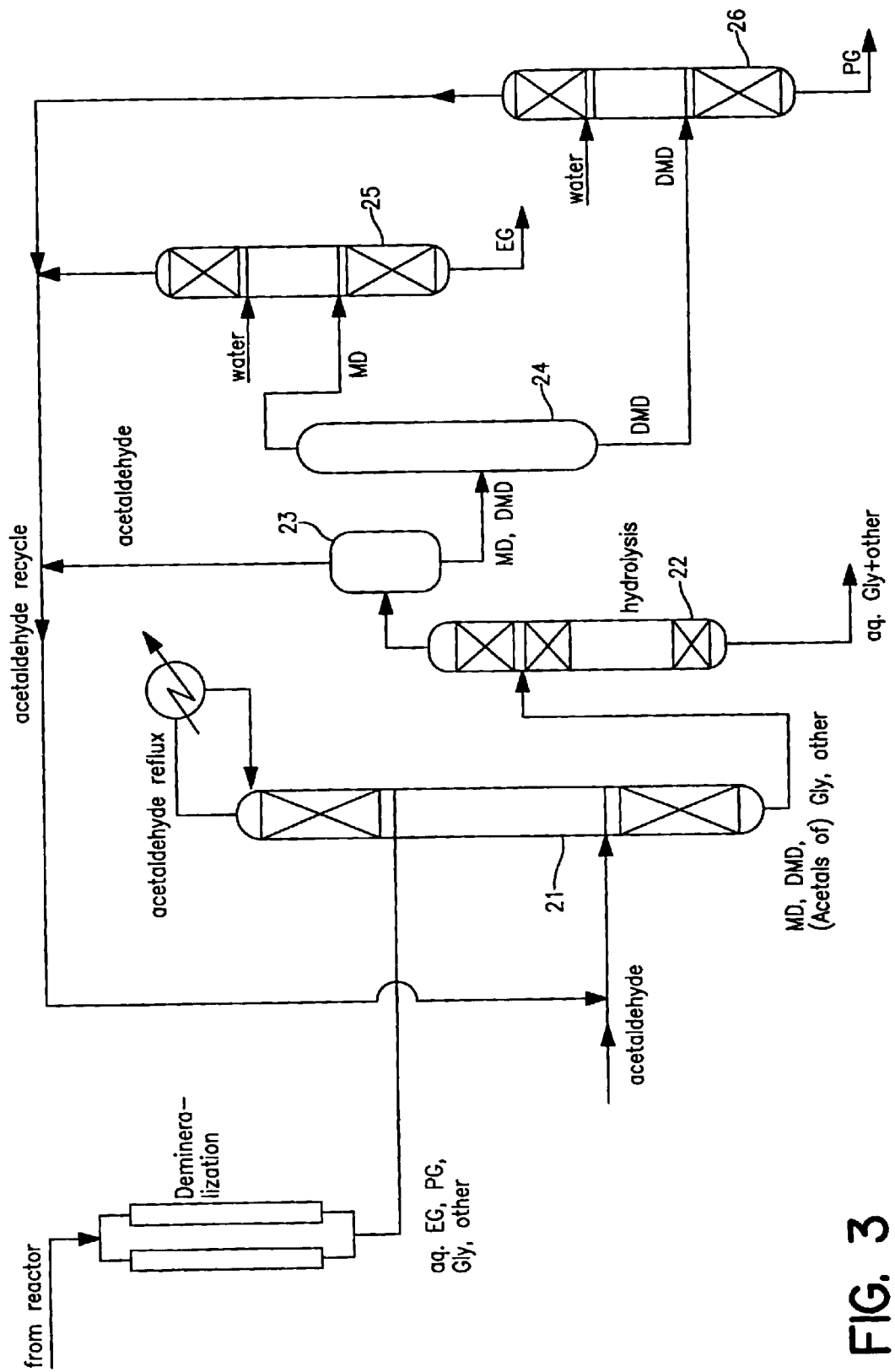
FIG. 3 is a schematic view of reactive distillation column 21 and acetal hydrolysis and polyol recovery columns 25 and 26 as an alternative to the process of FIG. 2 for the recovery of EG and PG.

FIG. 3 shows an alternate scheme where the acetals are recovered at the bottom of the reactive distillation column 21. The potential advantage of this scheme is that only a stoichiometric quantity of acetaldehyde would be needed for the acetalization. Acetals are separated in a second column 22 and then again separated from each other and subsequently hydrolyzed. The acetaldehyde is refluxed. Column 22 is for the hydrolysis of polyols other than 2MD, DMD (or other polyol components) with the separation of MD and DMD from acetaldehyde by a flash unit or column 23. The DMD is separated from MD in a multi-stage column 24 and the MD and DMD are separately hydrolyzed in recovery columns 25 and 26 to produce ethylene glycol and propylene glycol at high purity.

EXAMPLE 1

This Example uses a semi-batch reactor to show the feasibility of the reactive distillation scheme for separation of EG and PG from aqueous solutions. A typical composition of a product stream from a $C_5$ sugar alcohol hydrogenolysis reactor was chosen for these studies. As shown in Table 2, with formaldehyde as an acetalization agent in 50% excess, 98% recovery of EG and more than 99% recovery of PG was achieved. However, formaldehyde is less desirable as an acetalization chemical as previously discussed.

TABLE 2

Recovery of EG and PG via semi-batch acetalization and reactive distillation

| Species | Initial concentration in solution (wt %) | Final concentration in solution (wt %) (% removal in parenthesis) | |
|---|---|---|---|
| | | Run #1 | Run #2 |
| EG | 7.81 | 1.64 (79%) | 0.16 (98%) |
| PG | 11.04 | 0.23 (98%) | ~0.0 (99+%) |
| Glycerol | 1.54 | NA | NA |
| Xylitol | 4.62 | NA | NA |
| Total | 25.00 | | |

EXAMPLE 2

This Example shows the system used for separation and quantification of the products.

Figure 4:
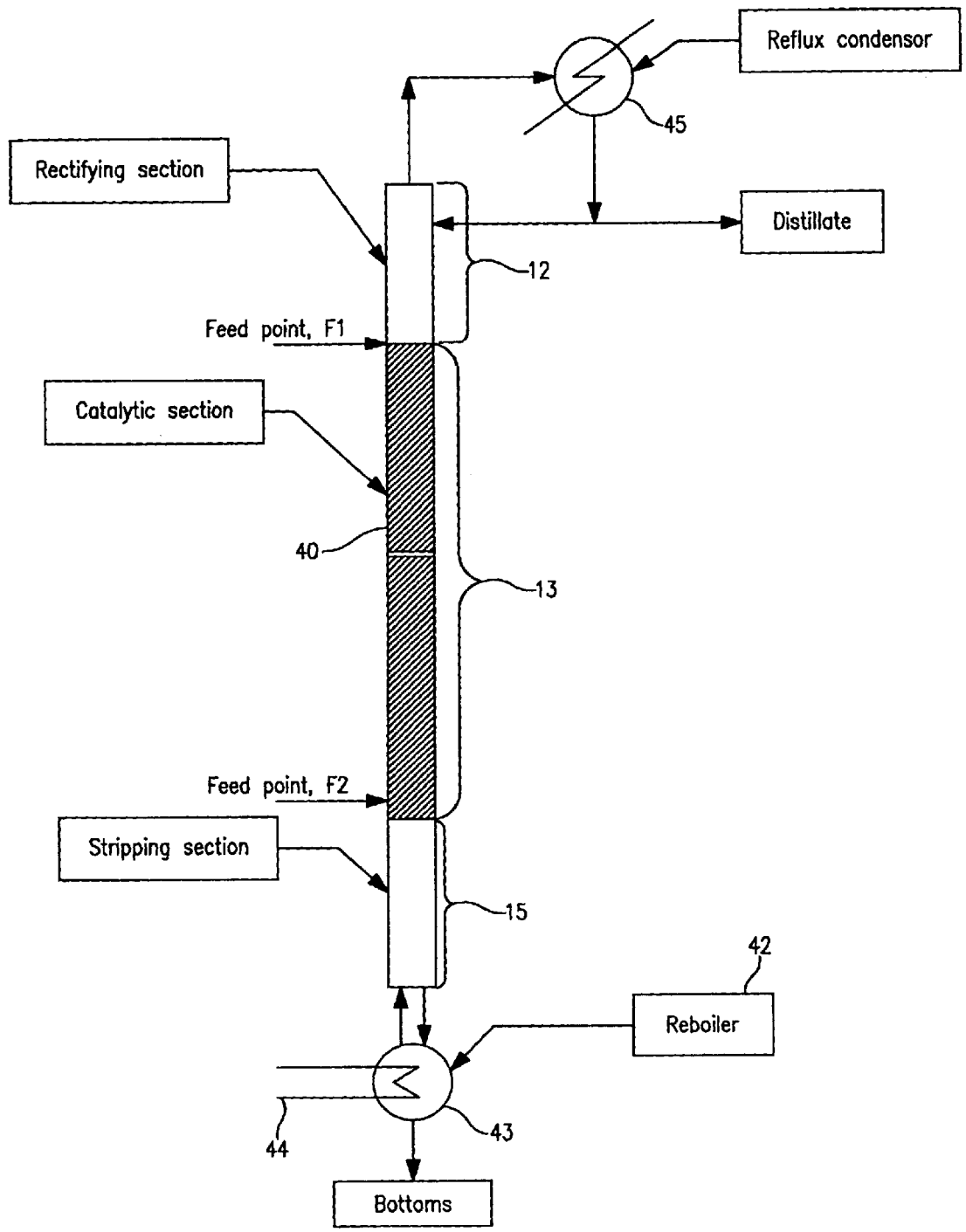
FIG. 4 shows the experimental column for Example 2.

Distillation column: As shown in FIG. 4, the column 40 consisted of a 2" (5.08 cm) diameter×7 ft (213.4 cm) tall Pyrex tube in 3' (36.25 cm) and 4' (121.92 cm) sections. The column 40 contained Katamax structured packing 41 from Koch-Glitsch, Ltd. (Wichita, Kans.); up to 15 elements were placed into the column for a total packed height of 82" (208.28 cm). The catalyst, a 1 mm ion exchange resin in acid form (Amberlyst 15™, Rhome & Haas), was contained in folded pouches inside each element. The column 40 was wrapped with heating tape (not shown) in two-foot sections; the temperature of each heating tape was controlled, with a surface thermocouple and Omega controller to near the internal column 40 temperature to minimize heat losses. At the bottom of the column reboiler 42 consisted of a 1000 ml round-bottom flask 43 held in a heating mantle 44; the reboiler 42 had an overflow level control to maintain a constant inventory in the reboiler flask. A glass reflux splitter 45 with a reflux condenser made up the top of the column 40; electronic timers control the reflux ratio at the desired value. The condenser was cooled by a 40 wt % solution of ethylene glycol circulated through a chiller to allow condenser temperatures as low as −20° C. Two feed pumps F1 and F2 dispense feed solutions to the column at a controlled rate from 1 to 200 ml/min. The column itself had 14 ports that allowed temperature measurements, introduction of feed, or sample withdrawal. The column had sections 12, 13 and 15 as shown in FIG. 1.

Analytical Method

Analysis techniques used liquid chromatography (HPLC) and gas chromatography (GC) for analysis of glycols and acetals. An improved GC method was the use of a slightly polar Porapak R packed column (6'×⅛" OD) that enabled the separation of glycols, acetals, water and acetaldehyde in one injection. The analysis was conducted in a Varian 3700 gas chromatograph equipped with a thermal conductivity detector and using helium carrier gas at a flow rate of 0.45 cm³/s. Column temperature was initially maintained at 140° C. for 2 minutes and then increased to 230° C. at a ramp rate of 45° C./min. The injector and detector block temperatures were maintained at 230 and 250° C., respectively. This method allows separation and quantification of water, acetaldehyde, 2MD, 24DMD, EG and PG. HPLC was used for analysis of glycols and other organic compounds produced in the bottom streams of the distillation. A Bio-Rad HPX-87H column with 0.005 M $H_2SO_4$ as a mobile phase, 50° C. column temperature, and refractive index detection was used.

EXAMPLE 3

Reaction equilibrium: Batch studies were carried out at several reaction temperatures to determine the reaction equilibrium for glycols recovery using acetaldehyde.

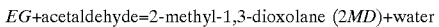

EG+acetaldehyde=2-methyl-1,3-dioxolane (2MD)+water

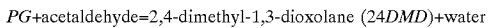

PG+acetaldehyde=2,4-dimethyl-1,3-dioxolane (24DMD)+water

The equilibrium constant for these reactions are given as

$K_e = C_{2MD} C_{H_2O} / C_{EG} C_{acetaldehyde}$

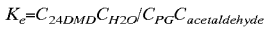

$K_e = C_{24DMD} C_{H_2O} / C_{PG} C_{acetaldehyde}$ where C is the concentration of the species in the reaction solution. The results of these experiments are given in Table 3 as a function of temperature. Also given in Table 3 is the equilibrium constant for the reaction of PG with acetone, taken from a paper by Chopade (Chopade, S., Reactive and Functional Polymers, vol. 42, p201 (1999)).

TABLE 3

Reaction equilibrium constants for acetal formation

| EG-Acetaldehyde | | PC-Acetaldehyde | | PG-Acetone | |
|---|---|---|---|---|---|
| T(° C.) | $K_e$ | T(° C.) | $K_e$ | T(° C.) | $K_e$ |
| 25 | 6.1 | 25 | 18.2 | 30 | 0.3 |
| 44 | 4.9 | 40 | 17 | 40 | 0.24 |
| 82 | 3.8 | 59 | 13.8 | | |
| | | 82 | 8.4 | | |

EXAMPLE 4

This Example describes VLLE data for two acetals and water, and vapor pressure data for the acetals. These thermodynamic data are important for determining the efficacy of the process.

Thermodynamic data for acetals and acetal/water mixtures Vapor-Liquid-Liquid Equilibrium (VLLE): An Othmer still, traditionally used for the collection of vapor-liquid equilibrium data (Othmer, D., Ind. & Eng. Chem. 20 743 (1928)), was used to facilitate the collection of VLLE data for the systems 2MD-water and 24DMD-water. The pure acetals used in the experiments were prepared by batch processing as follows: excess aldehyde was added to EG or PG, stirred in the presence of ion exchange resin for several hours, and then distilled to recover the acetal-water azeotrope. This azeotrope was then dried using molecular sieves to remove all water present. To determine VLLE data, specified quantities of acetal and water were placed in the Othmer still and brought to reflux. After steady state was reached, as evidenced by continuous reflux of the condensed vapor back into the still pot and a constant liquid temperature, samples of each liquid phase and condensed vapor were taken and analyzed as described above. The diagrams are thus generated by changing the mole fraction in the initial charge to the still across the entire composition range from zero to one.

Figure 5:
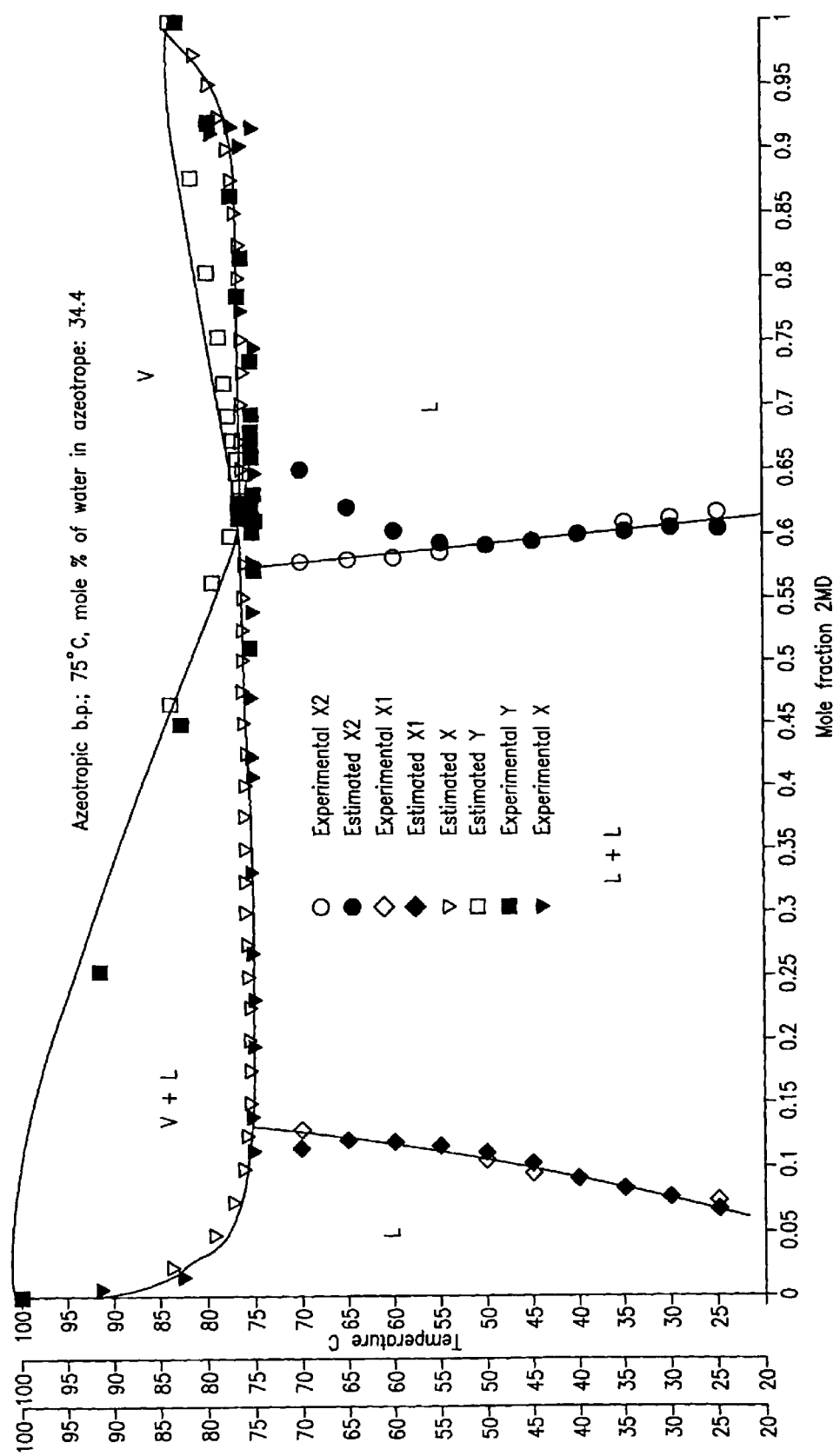
FIG. 5 is a graph showing a binary T-x-y vapor liquid-liquid equilibrium (VLLE) diagram for 2MD and water.
Figure 6:
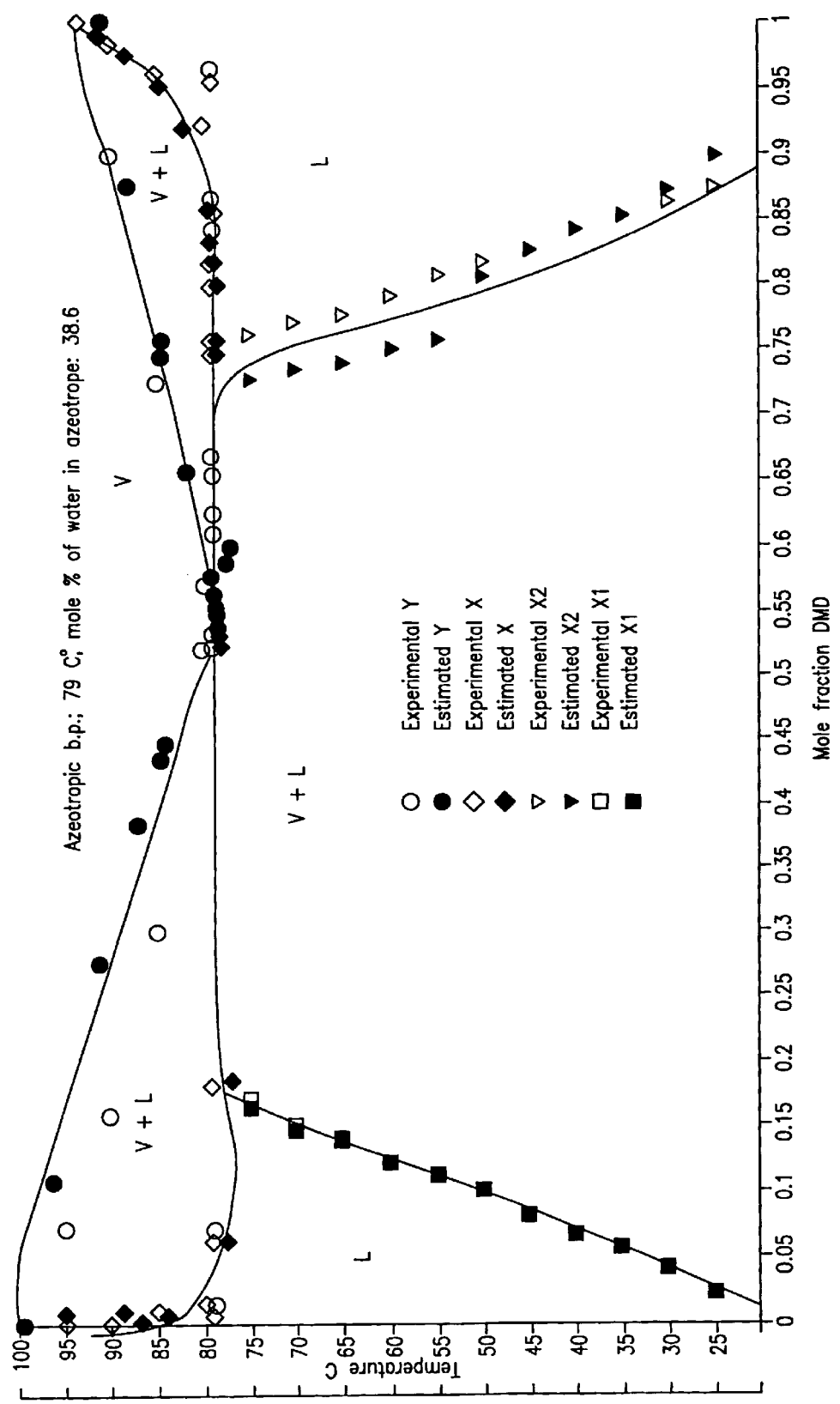
FIG. 6 is a binary T-x-y VLLE diagram for 24DMD and water.

The T-x-x-y diagrams for 2MD-water and 24DMD-water are given in FIGS. 5 and 6, respectively; these diagrams contain both the experimental data and the fit of the data as described below. Water and acetals are only partially miscible, so there are regions where two liquid phases are present (thus vapor-liquid-liquid information is required). In addition to the presence of two liquid phases, both acetals form minimum-boiling azeotropes with water. It is this minimum-boiling azeotrope that makes the technology especially attractive, as the lower boiling point at which the acetal can be recovered is advantageous.

Although the phase equilibrium is somewhat complex, it is possible to take advantage of these complexities to induce more efficient separations than would otherwise be possible. The VLLE data are important for understanding experiments, conducting process design, and modeling and conducting economic assessment of the technology.

The VLLE data for the acetal-water systems were fit to the UNIQUAC equation of state in order to facilitate more practical use of the data. The outputs from data regression include the estimated vapor-liquid data using UNIQUAC and the UNIQUAC binary interaction parameters. The estimated vapor-liquid data must be a close fit to the experimental vapor-liquid data in order to be of any use. FIGS. 5 and 6 show the comparison between the estimated and actual experimental equilibrium data for the systems of 2MD-water and 24DMD-water. Table 4 gives the UNIQUAC binary interaction parameters for each system.

TABLE 4

UNIQUAC Binary Interaction Parameters

| Component I | DMD | 2MD | DMD |
|---|---|---|---|
| Component J | Water | Water | Actaldehyde |
| Temperature | K | K | K |
| $A_{IJ}$ | −14.68 | 64.31 | −0.1225 |
| $A_{JI}$ | −56.15 | −80.00 | −0.1708 |
| $B_{IJ}$ | 3871.28 | 2305.94 | 244.763 |
| $B_{JI}$ | −3981.73 | −1339.78 | 450.817 |
| $C_{IJ}$ | −2.69 | −15.769 | −0.0280 |
| $C_{JI}$ | 16.97 | 18.214 | −0.0746 |
| $D_{IJ}$ | 0.0495 | 0.0567 | 0.000045 |
| $D_{JI}$ | −0.0904 | −0.0645 | −0.004122 |

Vapor pressure data: As with the acetal-water VLLE data, vapor pressure data are needed to assess the separation of the acetals and for simulation studies (such as the UNIQUAC fitting of VLLE data described above). Vapor pressure data for pure acetals were collected in a closed pressure vessel. Initially, a small quantity of pure acetal was placed in the vessel and the vessel was placed in an ice bath. When it was cooled, vacuum was applied to remove air, but not strongly enough to boil off the acetal. The initial pressure was noted, and then the closed assembly was put in a constant temperature water bath and allowed to equilibrate. The final pressure was recorded; the difference between the initial and final pressure is the vapor pressure at that temperature. The experiment was repeated at a number of temperatures.

Figure 7:
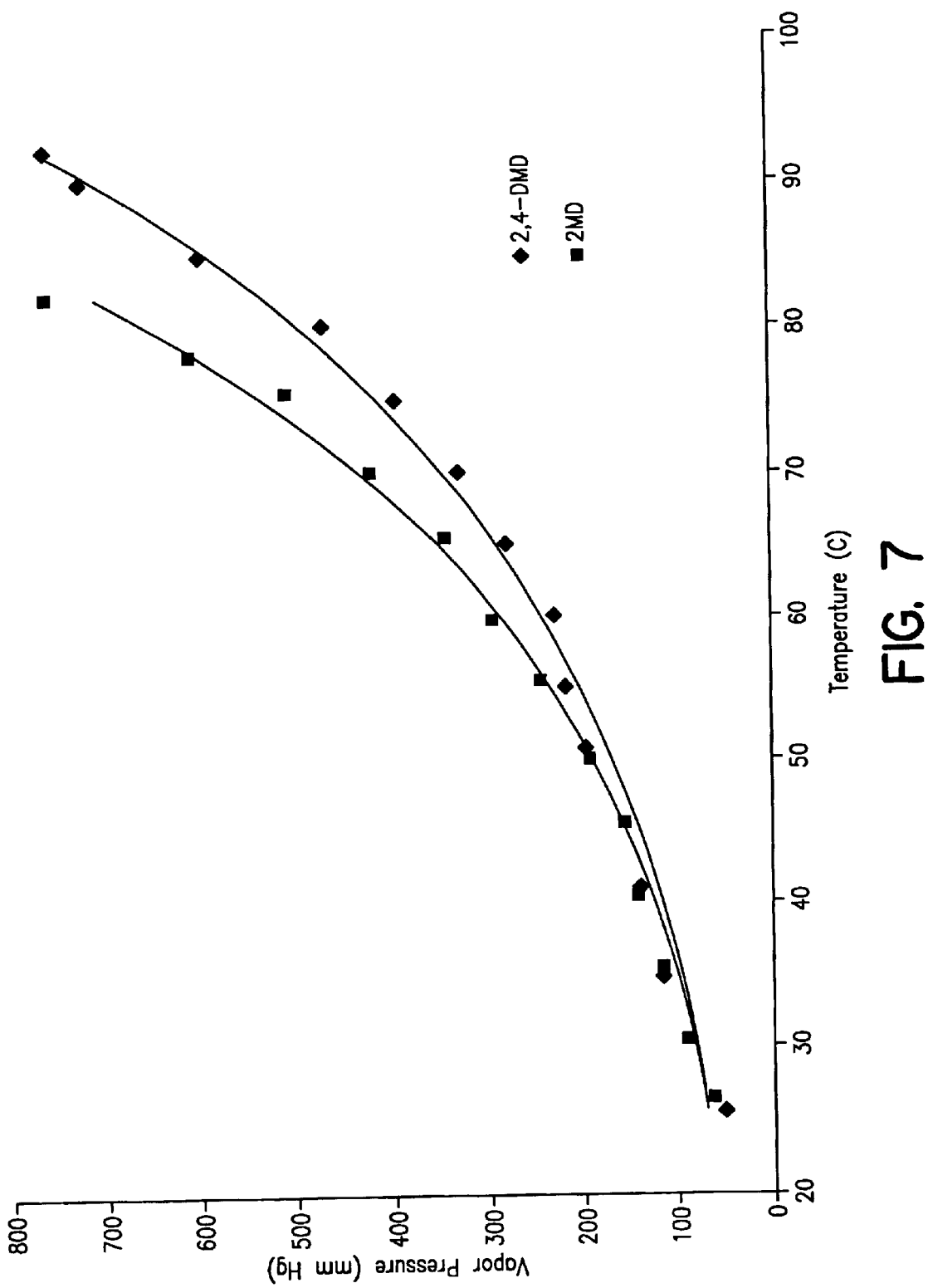
FIG. 7 is a graph showing vapor pressure data for DMD and MD at various temperatures. The data of FIGS. 5 to 7 was developed for the present invention.

The experimental vapor pressure data are shown in FIG. 7. The constants in Antoine's equation, which is the standard form used to characterize vapor pressure data, were calculated from the above experimental data. Further, the heat of evaporation was calculated from the vapor pressure data using the Clausius-Clapeyron equation. The Antoine's constants, predicted boiling point, and predicted heat of evaporation are given in Table 5. The predicted values agree very closely with the experimental values, thus verifying the accuracy of the experimental data.

TABLE 5

Predicted Antoine's constants and heat of vaporization of 2MD and 2,4-DMD a) Antoine's constant

| Dioxolane | A | B | C | Range (C) |
|---|---|---|---|---|
| MD | −19.6751 | 15909.9 | −688.602 | 25–80 |
| 2,4-DMD | −4.98443 | 3238.18 | −369.988 | 25–90 | b) Boiling points

| | | Predicted Boiling Point (C.) | |
|---|---|---|---|
| Dioxolane | Boiling point (C.) | Antoine's eqn. | Exponential graph |
| MD | 82–83 | 83.8 | 83.6 |
| 2,4-DMD | 92 | 91.26 | 91.8 | c) Predicted heat of vaporization by Clausius-Clapeyron equations

| Acetal | −Hv/R (K) | B | Expt calculated Hv(KJ/mol) | NIST (Reported) KJ/mol | Std Source (Reported) KJ/mol |
|---|---|---|---|---|---|
| 2MD | −4230.60 | 89.033 | 35.17322 | 35 | 34.32 |
| 2,4-DMD | −3684.16 | 62.33 | 30.63007 | NA | NA |

Separation of Acetals by Conventional Distillation

Figure 8:
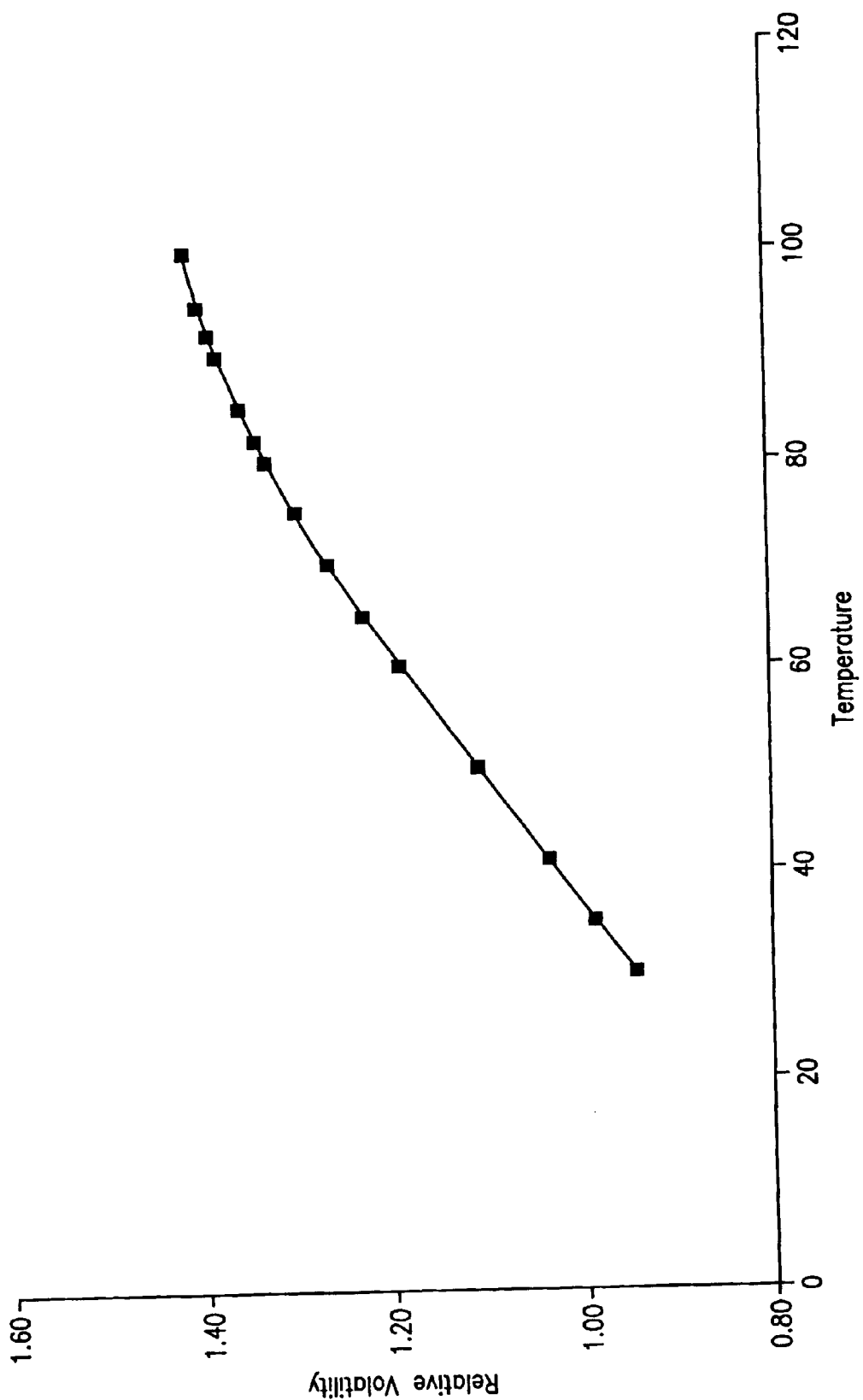
FIG. 8 is a graph showing a plot of relative volatility of MD/DMD vs temperature.

The ratio of the vapor pressures of the two acetals (from FIG. 7) is equal to the relative volatility of the 2MD to 24DMD if mixtures of the two are considered ideal. The plot of temperature versus relative volatility is shown in FIG. 8. At the temperature range over which separation of the two species would take place at atmospheric pressure (80–90° C.), the value of the relative volatility of 2MD and 24DMD is about 1.3. Thus, separation of 2MD from 24DMD is possible by fractional distillation.

An experiment to illustrate the separation of the two acetals was carried out in a small distillation column. The column consisted of a 1¼" diameter×5 ft tall Pyrex tube packed with wire mesh packing similar to FIG. 4. The column is wrapped with heating tape and the temperature of heating tape is controlled (with a surface thermocouple and Omega controller) to near the internal column temperature to minimize heat losses. The reboiler consists of a 500 ml roundbottom flask held in a heating mantle; the reboiler has an overflow level control to maintain a constant inventory in the reboiler flask. A glass reflux splitter with a reflux condenser makes up the top of the column; electronic timers control the reflux ratio at the desired value. The condenser is cooled by a 40 wt % solution of ethylene glycol circulated through a chiller to allow condenser temperatures as low as −20° C. The feed pumps dispense feed solutions to the middle of column at a controlled rate from 1 to 200 ml/min. The column has 5 ports that allow temperature measurements, introduction of feed, or sample withdrawal.

The experiment was conducted by placing an equimolar mixture of 2MD and 24DMD into the reboiler and then bringing the column to temperature at total reflux. At this condition, 99+% pure 2MD was obtained at the top of the column and 99+% 24DMD was obtained at the bottom of the column, respectively. This clearly indicated the feasibility of separation of these acetals in a single column.

EXAMPLE 5

Figure 9:
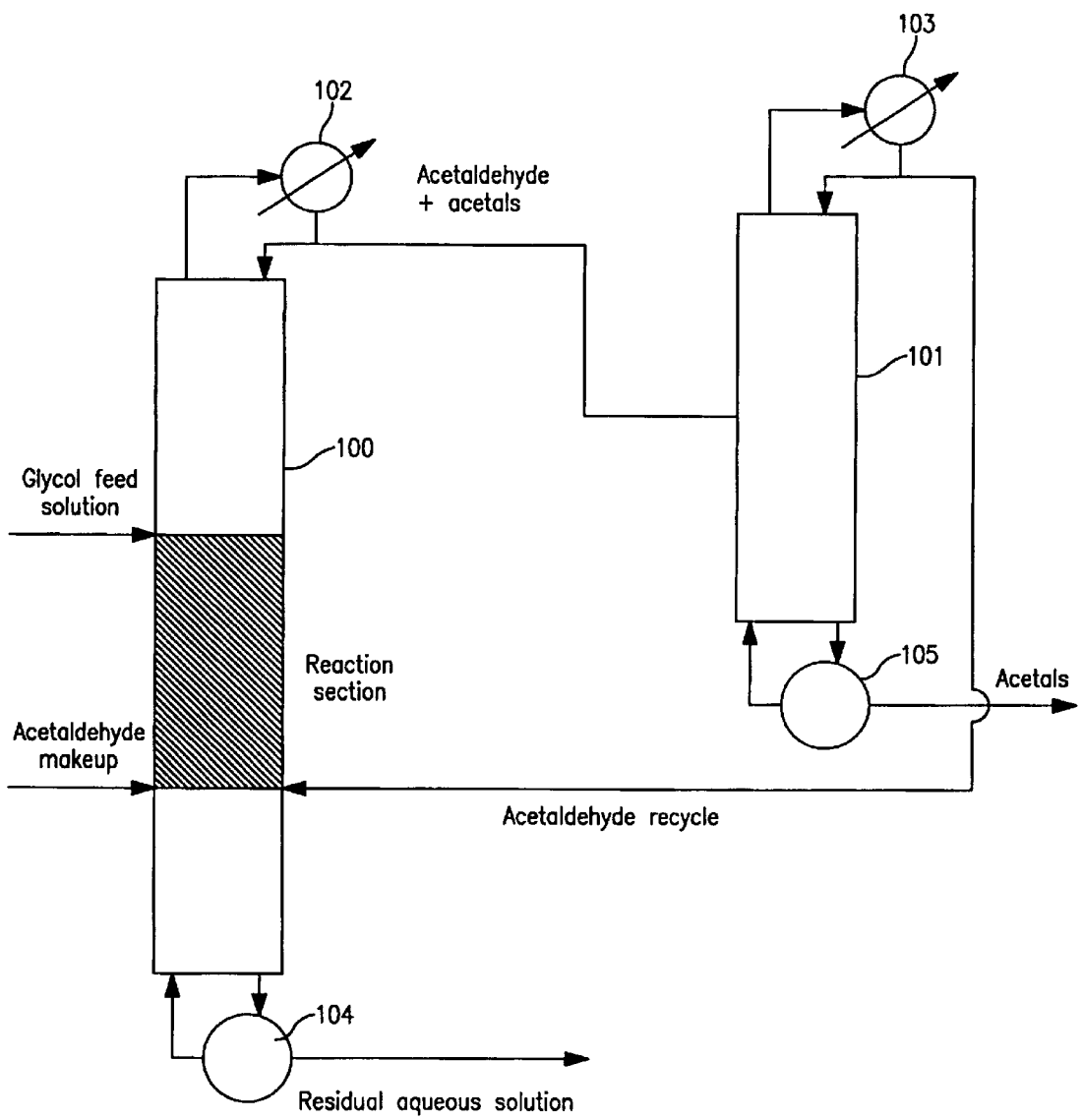
FIG. 9 is a process schematic showing two columns 100 and 101 for acetal formation in column 100 and for acetal recovery in column 101. The column 101 for recycle of acetaldehyde is on the right.

Continuous reactive distillation: FIG. 9 shows the two columns 100 and 101 used in Example 2. Column 100 is for the reactive distillation and column 101 is for the separation of the acetals from the acetaldehyde. Vessels 102 and 103 are reflux condensers and vessel 104 is the reboiler for vessel 100. Vessel 105 is a reboiler for vessel 101. This system allows for recycling acetaldehyde while maintaining favorable acetaldehyde and glycol molar ratios in column 100. Because acetaldehyde is so volatile and somewhat difficult to handle, a two-column system 100 and 101 was used for acetaldehyde-glycol studies to recycle acetaldehyde through the reactive distillation column 100. This system, shown schematically in FIG. 9, allows maintenance of high ratios of acetaldehyde to glycol (up to 10:1) in the column 100 while not consuming large quantities of acetaldehyde. Experiments were conducted to demonstrate acetal recovery in a reactive distillation column described in Example 2. The system PG-acetone was used initially for shakedown and to develop a familiarity with column 100 operation, because acetone has a boiling point of 58° C. (as opposed to acetaldehyde, which boils at 21° C.) and is easily handled at room temperature.

Results of the continuous reactive distillation experiments are given in Table 6.

2,2,4-trimethyl-1,3-dioxolane, was substantial only at high concentrations of PG (50%–100%) in the feed solution. These initial runs demonstrate that the ion exchange resin is active for acetal formation.

The experiments with EG-acetaldehyde and PG-acetaldehyde clearly demonstrate the feasibility of glycol recovery via acetal formation. In the run using 50% PG feed solution in water, 99% of PG is removed from the aqueous feed stream, leaving a bottoms product of essentially pure water. The recovery of EG is lower than for PG, corresponding to the lower reaction equilibrium conversion of EG to 2MD. The potential for increasing all recoveries is excellent, as these experiments were carried out with only 28" (71.12 cm) of catalyst section and moderate acetaldehyde recycle rates. Longer catalyst section would allow demonstration of nearly complete EG recovery.

The results compiled demonstrate the reactive distillation and recovery of polyols from aqueous solution.

EXAMPLE 6

This example shows a mixed feed solution of sorbitol, glycerol, EG, and PG. Only the acetals of EG and PG are removed in the top of the column, along with acetaldehyde. The bottoms consist of unreacted EG, PG, glycerol, sorbitol, and acetals of glycerol and sorbitol. The results are shown in Table 7.

TABLE 6

Results of continuous reactive distillation experiments

| System | Glycol feed concentration (Wt %) | Glycol solution feed rate (g/min) | Reflux ratio in column (L/D) | Height of catalyst section (in.) | Glycol concentration in bottoms (wt %) | Glycol conversion to acetal (%) |
|---|---|---|---|---|---|---|
| PG-acetone | 100 | 3.6 | 0.25 | 39 | 83 | 83 |
| PG-acetone | 75 | 3.6 | 0.25 | 39 | 63 | 47 |
| EG-acetaldehyde | 50 | 3.6 | 1 | 28 | 16 | 55 |
| EG-acetaldehyde | 50 | 6.0 | 1 | 28 | 29 | 42 |
| PG-acetaldehyde | 50 | 3.6 | 1 | 28 | 0.6 | 99 |
| PG-acctaldehyde | 25 | 3.6 | 0.75 | 28 | 1.4 | 94 |

The column operated as expected in initial shakedown runs using PG-acetone, but the formation of the acetal,

TABLE 7

Acetalization of simulated solution
*Table shows only top composition in mol %
Feed: 15% PG + 7% EG + 5% Glycerol + 5% Sorbitol (wt %)

| Run | Feed Position AcH | Feed Position (Solution) | Feed rate, AcH Mol/min | Molar feed ratio, Feed: AcH | Reflux ratio | Conv % PG (EG) | Top composition, mol % | | | | Bottom Composition, mol % | Temperature profile, C | | |
|---|---|---|---|---|---|---|---|---|---|---|---|---|---|---|
| | | | | | | | H2O | AcH | MD | DMD | | Top | Middle | Bottom |
| 1. | F2 | F1 | 0.101 | 1/6 | 1:4 | 52.28 18.47 | 25.94 | 61.23 | 2.33 | 10.50 | Mixture of unreacted feed | 48 | 68–101 | 101–103 |
| 2. | F2 | F1 | 0.119 | 1/5 | 1.4 | 34.20 11.94 | 49.14 | 42.24 | 1.72 | 6.89 | and their acetals of high boiling points (PG: 0.42%) (EG: 1.2%) | 65 | 85–101 | 101–103 |

Column Specifications: Enrichment section 15 cm, Reaction zone (with catalyst) 140 cm, Stripping section 45 cm
Feed position: F1, 15 cm from top; F2, 45 cm from top, and F, 45 cm from bottom.
(AcH: acetaldehyde, MD: 2-methyl dioxolane, DMD: 24 dimethyl 1,3 dioxolane; PG: Propylene glycol, EG: Ethylene glycol, H2O: water)
Feed rate: 0.02 mol/min
*At top there are only MD and DMD acetals

EXAMPLE 7

This Example shows the results with a feed solution containing a mixture of EG, PG and other polyols. There was no hydrolysis in section 14 of FIG. 1. The results are shown in the acetals of EG and PG produced. Small quantities of 4-ethyl-2-methyl-1,3-dioxolane (EMD), the acetal of 1,2-butanediol, were present at the top of the distillation column. The concentration of EMD will be reduced in a taller, commercial-scale system. No glycerol or sorbitol cyclic acetals were found in the PG or EG produced. The results are shown in Table 8.

TABLE 8

ACETALIZATION OF MIXED SOLUTION OF POLYOLS
Feed: 15% PG + 7% EG + 5% Glycerol + 5% Sorbitol + 2% 1–2 Butanediol (all in wt %)

| Run | Feed Position AcH | Feed Position (Solution) | Feed rate, AcH Mol/min | Molar feed ratio, Feed: AcH | Reflux ratio | Conv % PG (EG) | \multicolumn{5}{c}{Top composition, mol % From Column 11} | Bottom composition, mol % From Column 11 | \multicolumn{3}{c}{Temperature profile, C In Column 11} |
|---|---|---|---|---|---|---|---|---|---|---|---|---|---|---|---|
| | | | | | | | H2O | AcH | MD | DMD | EMD (Acetal of 2-butanediol) | | Top | Middle | Bottom |
| 1. | F2 | F1 | 0.119 | 1/6 | 1:4 | 53.27 25.39 | 29.31 | 54.97 | 3.63 | 12.04 | 0.023 | Mixture of unreacted feed and their acetals of high boiling points | 52 | 68–101 | 101–103 |
| 2. | F2 | F1 | 0.101 | 1/5 | 1.4 | 27.53 10.85 | 49.14 | 42.24 | 1.72 | 6.89 | 0.45 | | 70 | 82–101 | 101–103 |
| 3 | F2 | F1 | 0.082 | 1/4 | 1:4 | 57.78 28.28 | 21.03 | 54.96 | 5.67 | 18.28 | 0.03 | | 44 | 65–101 | 101–103 |
| 5. | F2 | F1 | 0.06 | 1/3 | 1:4 | 54.47 24.61 | 15.32 | 66.07 | 3.5 | 12.54 | 2.4 | | 50 | 66–101 | 101–103 |
| 4. | F2 | F1 | 0.119 | 1/6 | 1:4 | 69.22 31.44 | 14.1 | 67.58 | 8.95 | 29.21 | 0.09 | | 44 | 62–101 | 101–103 |
| | | | | | | (12) | (13) | | | | (15) | | | | |

Column Specifications: Enrichment section 15 cm, Reaction zone (with catalyst) 140 cm, Stripping section 45 cm; Length 200 cm
Feed position: F1, 15 cm from top; F2 45 cm from top, and F, 45 cm from bottom.
(AcH: acetaldehyde, MD: 2-methyl dioxolane, DMD: 24 dimethyl 1,3 dioxolane; EMD: 4-ethyl-2-methyl-1,3-dioxolane
PG: Propylene glycol, EG: Ethylene glycol, H2O: water)
(No glycerol or sorbitol cyclic acetals in product)
Feed rate: 0.02 mol/min

EXAMPLE 8

Example 8 shows the fractional distillation of DMD and MD mixtures with and without water. The distillate column was 1½" (3.8 cm) in diameter and 5 ft (152.4 cm) in length with wire mesh packings. The results in Tables 9 and 10 show that such separations are feasible.

TABLE 9

A) Distillation of mixture of pure components

| Run | Reflux ratio | Distillate composition, mol % | | Bottom composition, mol % | | Temperature profile, C | |
|---|---|---|---|---|---|---|---|
| | | MD | DMD | MD | DMD | Top | Bottom |
| 1 | Total Reflux | 81.56 | 18.44 | 0.0 | 99.999 | 83 | 102 |
| 2 | Total Reflux | 91.7 | 8.3 | 0.0 | 99.999 | 82 | 97 |

TABLE 10

B) Distillation in presence of water

| Run | Reflux ratio | Distillate composition, mol % | | | | Bottom composition, mol % | | | | | | Temperature profile, C | |
|---|---|---|---|---|---|---|---|---|---|---|---|---|---|
| | | MD | DMD | Water | AcH | MD | DMD | Water | AcH | EG | PG | Top | Bottom |
| 1 | Total Reflux | 57.17 | 3.01 | 39.36 | 0.00 | 17.80 | 82.19 | 0.0 | — | — | — | 75 | 92 |
| 2 | Total Reflux | 37.81 | 17.43 | 33.24 | 11.5 | 0.0 | 87.17 | 0.0 | 0.0 | 6.3 | 6.4 | 82 | 104 |

(At high temperature hydrolysis of acetal takes place)

EXAMPLE 9
Acetal Hydrolysis via Reactive Distillation

Having demonstrated that the acetals of EG and PG can be formed and recovered via reactive distillation using an ion exchange resin in acid form (Amberlyst 15), the hydrolysis of acetals in the reactive distillation column to obtain high purity propylene and ethylene glycol was examined. The emphasis was primarily to have high purity propylene glycol, specifically with a very low (ppm) level of acetaldehyde impurity. As part of this effort, process simulation software was used with the VLLE data to help design the lab experiments and verify the potential of obtaining high purity PG.

Hydrolysis of 2,4DMD: Initial experiments were carried out with a 100 cm reaction zone (packing with catalyst) and 200 cm of total structured packing (Katamax structured packing, Koch-Glitsch, Ltd., Wichita, Kans.). Because of substandard performance with 100 cm of reaction zone, later experiments were conducted with a 140 cm reaction zone and 200 cm total packing. The catalyst, 1 mm ion exchange resin beads in acid form (Amberlyst 15), is contained in folded pouches inside each element of the reaction zone. The details of the packing are mentioned in the previous Examples.

The column was operated under steady state at a variety of reflux ratios, temperature profiles, and water:acetal feed ratios. The experimental results are tabulated in Table 11.

TABLE 11

Hydrolysis of 2,4 Dimethyl dioxolane

| Run | Feed Position H2O | Feed Position DMD | Feed rate, DMD mol/hr | Molar feed ratio, DMD:H2O | Reflux ratio | Conv % (DMD) | Distillate composition, mol % | | | Bottom composition, mol % | | | Temperature profile, C | | |
|---|---|---|---|---|---|---|---|---|---|---|---|---|---|---|---|
| | | | | | | | H2O | AcH | DMD | H2O | DMD | PG | Top | Middle | Bottom |
| 1 | F2 | F | 1.99 | 1/2 | 1:2 | 64.29 | 15.59 | 67.87 | 16.13 | 69.61 | 0.00 | 30.38 | 42 | 82–98 | 98–103 |
| 2 | F2 | F | 1.99 | 1/2 | 1:2 | 72.89 | 40.51 | 47.09 | 12.38 | 77.70 | 0.00 | 21.17 | 64 | 86–99 | 100–106 |
| 3 | F1 | F | 1.99 | 1/2 | 1:2 | 77.22 | 17.02 | 65.59 | 16.98 | 79.24 | 0.00 | 20.75 | 56 | 84–98 | 99–105 |
| 4 | F1 | F | 1.99 | 1/2 | 1:4 | 80.13 | 17.06 | 66.28 | 16.65 | 78.41 | 0.00 | 21.58 | 54 | 84–98 | 99–105 |
| 5 | F1 | F | 1.99 | 1/1.2 | 1:4 | 81.7 | 13.12 | 73.40 | 13.46 | 65.12 | 0.00 | 34.75 | 54 | 84–98 | 99–106 |
| 6 | F1 | F | 1.99 | 1/1.5 | 1:4 | 81.11 | 23.78 | 63.07 | 13.13 | 69.00 | 0.00 | 30.99 | 54 | 84–98 | 99–106 |
| 7 | F1 | F | 1.99 | 1/3 | 1:4 | 79.54 | 20.88 | 66.46 | 12.65 | 80.09 | 0.00 | 19.05 | 54 | 84–98 | 99–106 |

Column Specifications: Enrichment section 15 cm, Reaction zone (with catalyst) 140 cm, Stripping section 45 cm
Feed position: F1, 15 cm from top; F2 45 cm from top, and F, 45 cm from bottom.

With 100 cm of reaction zone, conversion of 24DMD to PG of about 75% was obtained. With the longer reaction zone of 140 cm and a shorter rectifying section, which allows more residence time in the catalytic section, up to 80% DMD conversion was achieved. Process simulation predicts and experiments verify that a water:acetal ratio of 1.2 to 2 is sufficient; higher water:acetal ratios do not further improve column performance. Most importantly, the PG product coming from the bottom of the column is very pure as seen in Table 11.

TABLE 12

Hydrolysis of 2 Methyl dioxolane

| Run | Feed Position H2O | Feed Position MD | Feed rate, MD mol/hr | Molar feed ratio, MD:H2O | Reflux ratio | Conv % (MD) | Distillate composition, mol % | | | Bottom composition, mol % | | | Temperature profile, C | | |
|---|---|---|---|---|---|---|---|---|---|---|---|---|---|---|---|
| | | | | | | | H2O | AcH | MD | H2O | MD | EG | Top | Middle | Bottom |
| 1 | F1 | F | 2.67 | 1/2 | 1:4 | 80.0 | 21.7 | 73.90 | 4.30 | 71.04 | 0.00 | 28.95 | 54 | 98–102 | 104–108 |
| 2 | F1 | F | 2.67 | 1/3.8 | 1:4 | 81.5 | 15.9 | 78.20 | 5.92 | 84.14 | 0.00 | 15.85 | 48 | 96–99 | 104–108 |
| 3 | F1 | F | 2.67 | 1/2 | 1:4 | 91.7 | 20.6 | 65.50 | 13.80 | 74.12 | 0.00 | 27.87 | 40 | 96–99 | 104–108 |
| 4 | F1 | F | 2.67 | 1/3 | 1:4 | 96.0 | 17.6 | 77.95 | 4.47 | 77.34 | 0.00 | 22.65 | 40 | 96–100 | 104–110 |
| 5 | F1 | F | 2.67 | 1/4 | 1:4 | 93.4 | 18.06 | 75.66 | 6.27 | 82.43 | 0.01 | 16.35 | 44 | 96–101 | 104–108 |
| 6 | F1 | F | 2.67 | 1/1.2 | 1:4 | 88.3 | 19.5 | 75.50 | 4.99 | 65.38 | 0.00 | 34.61 | 42 | 96–101 | 105–120 |

Column Specifications: Enrichment section 15 cm, Reaction zone (with catalyst) 140 cm, Stripping section 45 cm
Feed position: F1, 15 cm from top; and F, 45 cm from bottom.

Hydrolysis of 2MD: In experiments parallel to those described above for 24DMD, hydrolysis of 2MD was studied. The experimental results are summarized in Table 12, and show that higher conversions of 2MD to EG, up to 95%, can be achieved than for 24DMD to PG.

TABLE 13

Hydrolysis of mixed acetal (2MD and 2,4 DMD)

| Run | Feed Point (H2O) | Feed Point Acetal | Feed rate, mol/h DMD + MD | Molar feed ratio, DMD + MD:H2O | Reflux ratio | Conv % DMD (MD) | Top composition, mol % | | | | Bottom composition, mol % | | | | | Temperature profile, C | | |
|---|---|---|---|---|---|---|---|---|---|---|---|---|---|---|---|---|---|---|
| | | | | | | | H2O | AcH | MD | DMD | H2O | MD | DMD | EG | PG | Top | Middle | Bottom |
| 1 | F1 | F | 2.24 | 1/2.5 | 1:4 | 75.92 91.03 | 49.82 | 31.03 | 2.2 | 16.96 | 77.5 | 0.0 | 0.0 | 9.51 | 12.97 | 60 | 98–102 | 100–112 |
| 2 | F1 | F | 2.24 | 1/2.5 | 1:4 | 83.7 89.9 | 10.35 | 78.17 | 1.37 | 10.10 | 82.65 | 0.0 | 0.001 | 6.86 | 10.48 | 43 | 97–98 | 99–107 |
| 3 | F1 | F | 2.24 | 1/2.5 | 1:4 | 86.69 90.48 | 13.32 | 76.14 | 1.43 | 9.38 | 71.36 | 0.0 | 0.0 | 11.15 | 17.48 | 48 | 97–99 | 100–110 |
| 5 | F1 | F | 2.24 | 1/4.1 | 1:4 | 87.8 92.4 | 9.5 | 82.35 | 0.5 | 7.6 | 83.15 | 0.0 | 0.0 | 6.5 | 10.25 | 43 | 97–98 | 99–107 |
| 4 | F1 | F | 2.24 | 1/1.2 | 1:4 | 78.06 86.96 | 17.42 | 69.62 | 1.34 | 11.55 | 72.01 | 0.0 | 0.0 | 11.33 | 16.65 | 50 | 98–101 | 101–120 |

Feed: 62% mole DMD and 38% mole MD
Column Specifications: Enrichment section 15 cm, Reaction zone (with catalyst) 140 cm, Stripping section 45 cm
Feed position: F1, 15 cm from top; F2 45 cm from top, and F, 45 cm from bottom.

This is because the reaction equilibrium for hydrolysis of the acetal of EG is more favorable than that for hydrolysis of the acetal of PG. The reaction equilibrium constants are tabulated in Table 3.

The conversion of acetal to glycol in hydrolysis is limited in these examples by the height of packing available in the laboratory-scale column. With a longer reactive zone, complete hydrolysis of the acetal will take place. This is supported by the process simulations set forth hereinafter.

Figure 10:
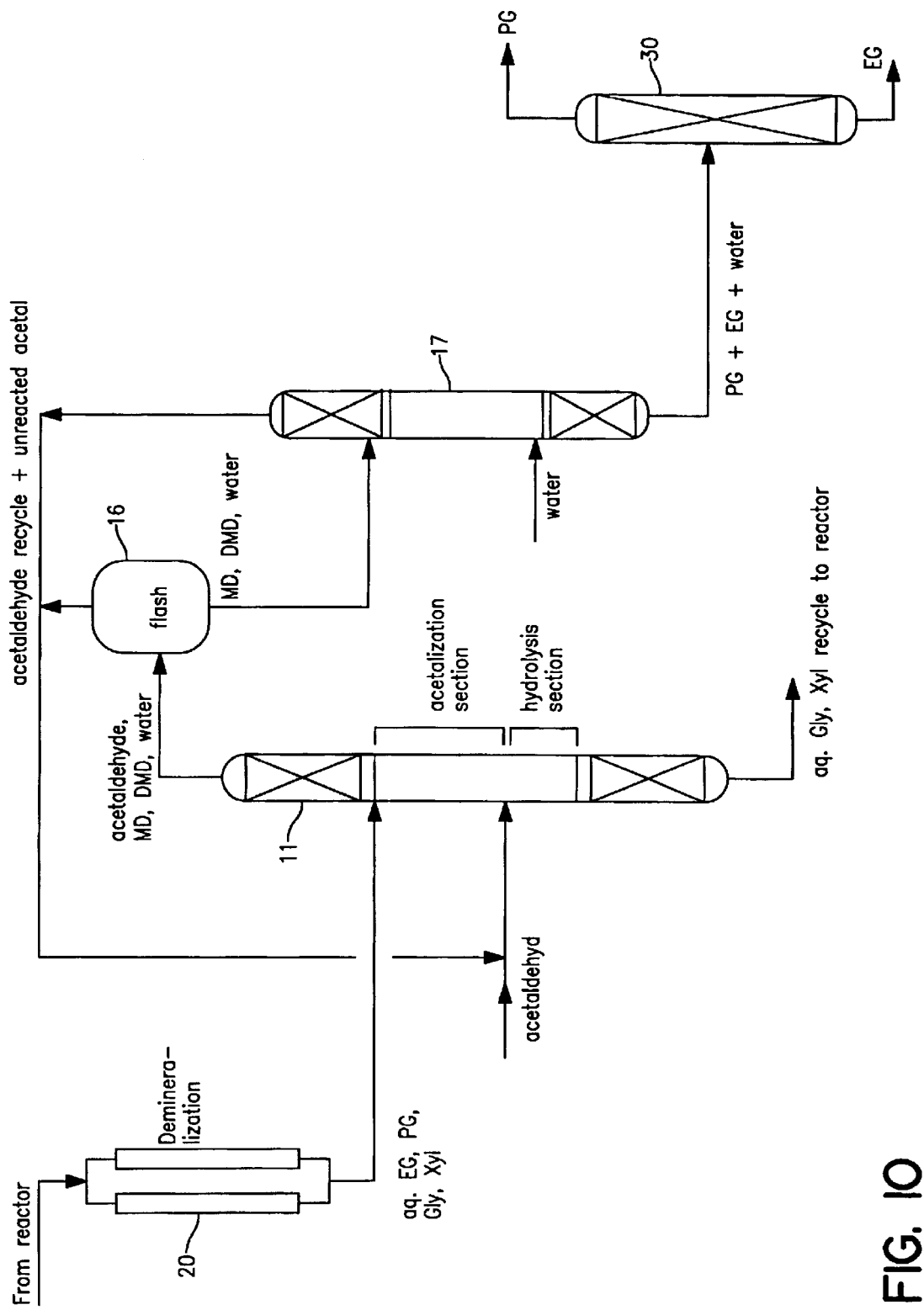
FIG. 10 is a schematic diagram similar to FIG. 2, except that the PG and EG are separated by distillation in column 30 after hydrolysis of the mixed acetals in column 17.

Alternative mixed acetal hydrolysis scheme: In an alternative scheme for the separation and hydrolysis of the acetals formed in reactive distillation, a mixture of both acetals are first hydrolyzed in one reactive distillation column and then the resulting mixture of PG and EG is separated in a conventional distillation column. This route can potentially reduce the number of distillation columns required from three to two, with only one reactive distillation column versus two in the original concept. This alternate route involves the separation of EG from PG, which is practiced commercially but is a difficult, expensive separation. This alternate scheme is shown as columns 29 and 30 in FIG. 10.

The hydrolysis of mixed acetals (2MD and 24DMD) was carried out in the same reactive distillation column as described above for individual acetal hydrolysis. Experiments were performed with mixtures of acetals only and with the acetals with water; mixture compositions were chosen to simulate the products from the acetal formation column. The results are tabulated in Tables 13 and 14 as a function of water: acetal ratio and reflux ratio.

TABLE 14

Hydrolysis of mixed acetal (2MD and 2,4 DMD) along with water

| Run | Feed Point (H2O) | Feed Point Acetal | Feed rate, mol/h DMD + MD | Over all Molar feed ratio, DMD + MD:H2O | Reflux ratio | Conv % DMD (MD) | Top composition, mol % | | | |
|---|---|---|---|---|---|---|---|---|---|---|
| | | | | | | | H2O | AcH | MD | DMD |
| 6 | F1 | F | 2.17 | 1/2.75 | 1:4 | 81.14 93.68 | 20.34 | 63.20 | 2.34 | 14.12 |
| 7 | F1 | F | 2.17 | 1/3.1 | 1:4 | 84.68 89.9 | 10.93 | 77.85 | 1.53 | 9.68 |

| Run | Bottom Composition, mol % | | | | | Temperature profile, C. | | |
|---|---|---|---|---|---|---|---|---|
| | H2O | MD | DMD | EG | PG | Top | Middle | Bottom |
| 6 | 81.86 | 0.0 | 0.0 | 8.33 | 9.8 | 44 | 97–99 | 100–110 |
| 7 | 80.53 | 0.0 | 0.0 | 8.5 | 10.88 | 46 | 96–99 | 100–110 |

Feed: 52% mole DMD and 33% mole MD + 15% mole H₂O
Column Specifications: Enrichment section 15 cm, Reaction zone (with catalyst) 140 cm, Stripping section 45 cm
Feed position: F1, 15 cm from top; F2 45 cm from top, and F, 45 cm from bottom.

Up to 95% conversion of 2MD and 85% conversion of 24DMD, values even slightly higher than those for the individual acetals, were achieved at optimum conditions. These results are promising and indicate that mixed acetal hydrolysis is a viable alternative to the original concept of separating acetals prior to hydrolysis.

Process Simulation of Hydrolysis

Computer process simulation software (Aspen Plus 10.1, Aspentec, Inc.) was used to model the proposed reactive distillation hydrolysis process. These simulations were conducted in part to help define experimental parameters for developmental studies, and more importantly to demonstrate the behavior of commercial scale processes particularly regarding product purities. Process simulation provides a means, based on experimental findings and thermodynamic (e.g. VLLE) data, to predict with significant confidence the performance of the proposed separation technology at the commercial level.

TABLE 15

Simulation results for single acetal (2,4 DMD) hydrolysis scheme

| | 1 Feed | 2 Feed | 3 Distillate | 4 Bottoms |
|---|---|---|---|---|
| Mole Flow kmol/hr | | | | |
| Water | 60 | 0 | 10 | 1.28E−04 |
| Acetaldehyde | 0 | 0 | 50.00 | 5.37E−16 |
| Propylene Glycol | 0 | 0 | 2.56E−11 | 49.99987 |
| DMD | 0 | 50 | 1.28E−04 | 1.43E−19 |
| Total Flow KMOL/HR | 60 | 50 | 60 | 50 |
| Temperature K | 298.2 | 298.2 | 330.5 | 460.9 |

| | |
|---|---|
| Number of Stages | 20 |
| Reflux Ratio | 3 |
| Boilup Ratio | 7 |
| Water Feed Location | 2 |
| DMD Feed Location | 7 |
| HETP (m) | 0.5 |
| Reaction Zone | Stage 5–15 |
| Packed Zone | Stage 5–15 |
| Packing | Kerapak |
| Packing Height (m) | 5.5 |
| Column Diameter (m) | 1.78 |

Figure 11:
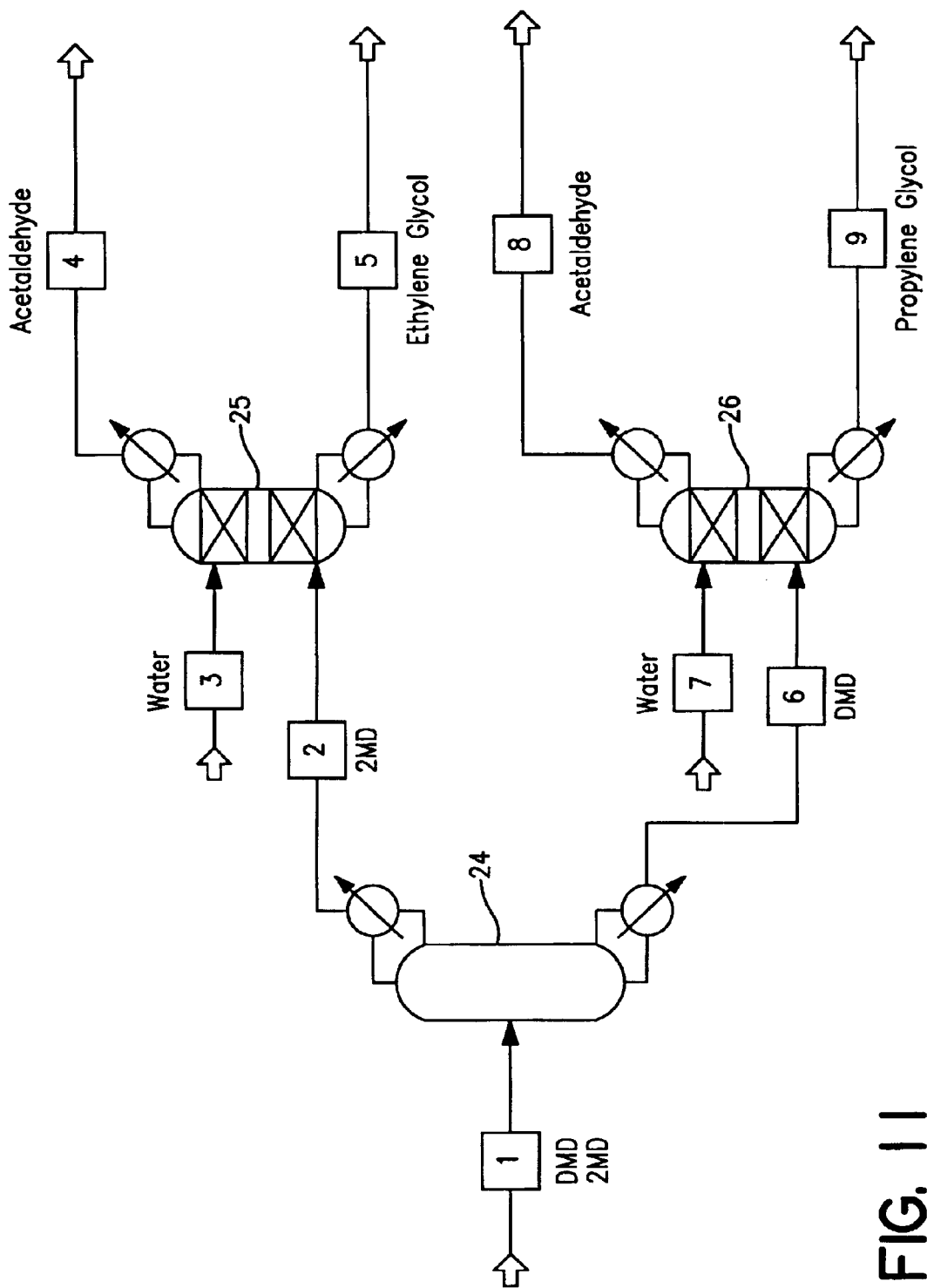
FIG. 11 is an additional view of the hydrolysis portion of the process, shown as vessels 17, 18 and 19 shown in FIG. 2.

The simulation results of 24DMD hydrolysis to PG, corresponding to column 26 in FIG. 11, are given in Table 15.

The parallel results for 2MD hydrolysis to EG, corresponding to column 25 in FIG. 11, are given in Table 16.

TABLE 16

Simulation results for single acetal (2MD) hydrolysis scheme

| | 1 Feed | 2 Feed | 3 Distillate | 4 Bottoms |
|---|---|---|---|---|
| Mole Flow kmol/hr | | | | |
| Water | 60 | 0 | 10 | 5.57E−08 |
| Ethylene Glycol | 0 | 0 | 7.79E−17 | 50 |
| Acetaldehyde | 0 | 0 | 50 | 5.00E−29 |
| 2MD | 0 | 50 | 5.57E−08 | 5.00E−29 |
| Total Flow KMOL/HR | 60 | 50 | 60 | 50 |
| Temperature K | 298.15 | 298.15 | 330.4646 | 470.2331 |

| | |
|---|---|
| Number of Stages | 25 |
| Reflux Ratio | 3.5 |
| Packing Height (m) | 8 |
| Column Diameter (m) | 1.71 |

The columns described in Tables 15 and 16 produce approximately 60 million lb mol of propylene glycol and 50 million lb mol of ethylene glycol per year; the column diameters are 1.78 m for the 24DMD hydrolysis column and 1.71 m for the 2MD hydrolysis column. Each column has been optimized to reduce the number of equilibrium stages until the maximum allowable amount of water is present in the glycol product stream in accordance with industry standards. Water:acetal feed ratios were reduced to slightly above the stoichiometric molar ratios to reduce operating costs of the condenser and reboiler. Inlet stream temperatures were set at room temperature to mimic experimental conditions. Emphasis was placed on reducing the level of acetaldehyde in the glycol product streams to the order of part-per-million levels. It is seen that the acetaldehyde content in all of the glycol product streams is negligible, indicating that very high purity PG and EG with reasonable column sizes (~25 stages) in a commercial process can be obtained.

The simulation results of mixed acetal hydrolysis are given in Table 17.

TABLE 17

Simulation results for mixed acetal hydrolysis scheme

| | 1 Feed | 2 Feed | 3 Distillate 1 | 4 Bottoms 1 | 5 Distillate 2 | 6 Bottoms 2 |
|---|---|---|---|---|---|---|
| Mole Flow kmol/hr | | | | | | |
| Water | 83.1586 | 28.34952 | 1.70E+00 | 2.43E−04 | 2.43E−04 | 3.69E−35 |
| Acetaldehyde | 0 | 0 | 109.8069 | 1.01E−14 | 0 | 0 |
| Propylene Glycol | 0 | 0 | 5.30E−11 | 68.22761 | 68.22689 | 7.13E−04 |
| Ethylene Glycol | 0.00E+00 | 0 | 6.02E−15 | 41.5793 | 3.27E−04 | 41.57897 |
| DMD | 68.22785 | 0 | 2.43E−04 | 2.09E−14 | 0 | 0 |
| 2MD | 41.5793 | 0 | 1.21E−08 | 1.10E−28 | 0 | 0 |
| Total Flow KMOL/HR | 192.9658 | 28.34952 | 111.5081 | 109.8072 | 68.22747 | 41.57969 |
| Temperature K. | 3.51E+02 | 3.48E+02 | 295.3956 | 4.64E+02 | 4.61E+02 | 4.70E+02 |

| | Column 1 | Column 2 |
|---|---|---|
| Number of Stages | 30 | 123 |
| Reflux Ratio | 5 | 12 |
| Boilup Ratio | 4.51 | 21.8 |
| Water Feed Location | 2 | — |
| Mixed Feed Location | 12 | 51 |
| HETP (m) | 0.5 | — |
| Reaction Zone | Stage 2–15 | — |
| Packed Zone | Stage 2–20 | 0.609 m/stg |

TABLE 17-continued

| Simulation results for mixed acetal hydrolysis scheme | | |
|---|---|---|
| Packing/Trays | Kerapak | Sieve |
| Packing/Col Height (m) | 9.5 | 74.9 |
| Column Diameter (m) | 2.14 | 2.8 |

This hydrolysis column was optimized in the same manner as the single acetal hydrolysis. It also produces approximately 60 million lb mol of propylene glycol and 50 million lb mol of ethylene glycol per year. The column diameter of the mixed acetal hydrolysis is 2.14 m, somewhat larger than the single acetal hydrolysis columns. The second column to separate EG and PG via conventional distillation is very large. Again, a negligible quantity of acetaldehyde is present in the product mixed glycol stream, indicating that pure EG and PG can be produced in a commercial-scale process.

Summary

The combined results of experimental findings and simulation studies show the feasibility of reactive distillation for polyols recovery from aqueous solution. In particular, two viable scenarios are presented here for the separation and hydrolysis of acetals produced in reactive distillation to pure PG and EG. Experimental findings are in accordance with thermodynamic and reaction data, but experimental conversion and product purities are limited by the size (particularly the height) of the laboratory-scale equipment. Simulation studies, based on experimental data, demonstrate with a high degree of confidence that the required product purities and recoveries can be achieved in commercial-scale equipment.

It is intended that the foregoing description be only illustrative of the present invention and that the present invention be limited only by the hereinafter appended claims.

We claim:

1. A continuous process for preparing at least one cyclic acetal from an aqueous solution having at least one polyol and at least one other organic compound which forms another cyclic acetal by-product in the process which comprises:

(a) reacting in a combination reaction and distillation vessel a reaction mixture of the polyol, organic compound, and an aldehyde or ketone containing 1 to 4 carbon atoms in the aqueous solution in the presence of an acid catalyst, wherein the reaction mixture is introduced into the reaction vessel containing the catalyst with a molar excess of the aldehyde or ketone over the polyol to produce the cyclic acetal and cyclic acetal by-product in the aqueous solution; and (b) separating at least one cyclic acetal from the reaction mixture containing the at least one cyclic acetal by-product by distillation.

2. The process of claim 1 wherein there is more than one polyol in the reaction mixture which is reacted.

3. The process of claim 1 wherein the reaction mixture contains ethylene glycol and propylene glycol as polyols which react with the aldehyde in the mixture to form the cyclic acetal.

4. The process of any one of claims 1, 2 or 3 wherein the reaction mixture contains at least one of glycerol, sorbitol, and C4 diols and triols as the other organic compound which react with the aldehyde to form additional cyclic acetals which have a higher boiling point than the cyclic acetal distilled from the reaction mixture.

5. The process of claims 1, 2 or 3 wherein in addition the excess aldehyde or ketone is recycled to step (a).

6. The process of any one of claims 1, 2 or 3 wherein acid catalyst in step (a) is an acidic resin.

7. The process of any one of claims 1, 2 or 3 wherein the aldehyde in step (a) is acetaldehyde.

8. The process of claims 1, 2 or 3 wherein the cyclic acetal and the aldehyde or ketone are distilled from the reaction mixture.

9. The process of claims 1, 2 or 3 wherein the reaction mixture contains cyclic acetals of at least two polyols which are separated from the reaction mixture together, then separated from each other and then hydrolyzed separately to the polyols.

10. The process of any one of claims 1, 2 or 3 wherein the reaction mixture is at a temperature, less than the boiling point of the reaction mixture, at which the aldehyde or ketone is distilled from the reaction mixture.

\* \* \* \* \*